(12) United States Patent
Adachi et al.

(10) Patent No.: US 8,157,740 B2
(45) Date of Patent: Apr. 17, 2012

(54) CAPACITIVE MICROMACHINED ULTRASONIC TRANSDUCER (CMUT) DEVICE AND IN-BODY-CAVITY DIAGNOSTIC ULTRASOUND SYSTEM

(75) Inventors: Hideo Adachi, Iruma (JP); Atsushi Ohsawa, Tokyo (JP); Katsuhiro Wakabayashi, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 781 days.

(21) Appl. No.: 12/039,170

(22) Filed: Feb. 28, 2008

(65) Prior Publication Data

US 2008/0294055 A1 Nov. 27, 2008

(30) Foreign Application Priority Data

Mar. 29, 2007 (JP) ................................ 2007-087769

(51) Int. Cl.
*A61B 8/14* (2006.01)
(52) U.S. Cl. ........................................ 600/463; 600/459
(58) Field of Classification Search .................... 338/42;
257/416; 73/724; 600/416, 443, 447, 459,
600/467; 329/304; 310/334; 327/205; 324/686;
136/203; 455/255
See application file for complete search history.

(56) References Cited

U.S. PATENT DOCUMENTS

| | | | | |
|---|---|---|---|---|
| 4,498,070 A | * | 2/1985 | Lirman | 338/42 |
| 5,241,209 A | * | 8/1993 | Sasaki | 257/416 |
| 5,431,057 A | * | 7/1995 | Zimmer et al. | 73/724 |
| 5,583,290 A | * | 12/1996 | Lewis | 73/514.18 |
| 7,041,061 B2 | * | 5/2006 | Kramer et al. | 600/508 |
| 2002/0082501 A1 | * | 6/2002 | Emery | 600/443 |
| 2004/0147290 A1 | * | 7/2004 | Kikuchi | 455/562.1 |
| 2004/0178845 A1 | * | 9/2004 | Kouwenhoven et al. | 329/304 |
| 2005/0094490 A1 | * | 5/2005 | Thomenius et al. | 367/155 |
| 2005/0096546 A1 | * | 5/2005 | Hazard et al. | 600/447 |
| 2005/0146247 A1 | * | 7/2005 | Fisher et al. | 310/334 |
| 2005/0215909 A1 | * | 9/2005 | Barnes | 600/459 |
| 2006/0145059 A1 | * | 7/2006 | Lee et al. | 250/214 R |
| 2006/0158236 A1 | * | 7/2006 | Kozawa | 327/205 |
| 2006/0264758 A1 | * | 11/2006 | Hossack et al. | 600/467 |
| 2006/0273805 A1 | * | 12/2006 | Peng et al. | 324/686 |
| 2006/0278264 A1 | * | 12/2006 | Lin | 136/203 |
| 2007/0010225 A1 | * | 1/2007 | Oosawa et al. | 455/255 |
| 2007/0016055 A1 | * | 1/2007 | Cao et al. | 600/459 |
| 2007/0083119 A1 | | 4/2007 | Adachi et al. | |
| 2007/0167786 A1 | * | 7/2007 | Lee et al. | 600/447 |

FOREIGN PATENT DOCUMENTS

| | | |
|---|---|---|
| JP | 02-051073 | 2/1990 |
| JP | 2001-339796 | 12/2001 |
| JP | 2003-294527 | 10/2003 |
| JP | 2005-510264 | 4/2005 |
| JP | 2005-265432 | 9/2005 |
| JP | 2006-319713 | 11/2006 |
| WO | WO 03/011749 A2 | 2/2003 |
| WO | 2005/120359 A1 | 12/2005 |

* cited by examiner

*Primary Examiner* — Brian Casler
*Assistant Examiner* — Michael N Fisher
(74) *Attorney, Agent, or Firm* — Scully, Scott, Murphy & Presser, P.C.

(57) ABSTRACT

A capacitive micromachined ultrasonic transducer (cMUT) device, includes: a cMUT obtained by processing a silicon substrate by using a silicon micromachining technique; and an oscillator circuit having the cMUT as a capacitor, and outputting a frequency modulation signal by modulating a frequency of an oscillation signal to be output on the basis of a change of capacitance of the cMUT.

11 Claims, 10 Drawing Sheets

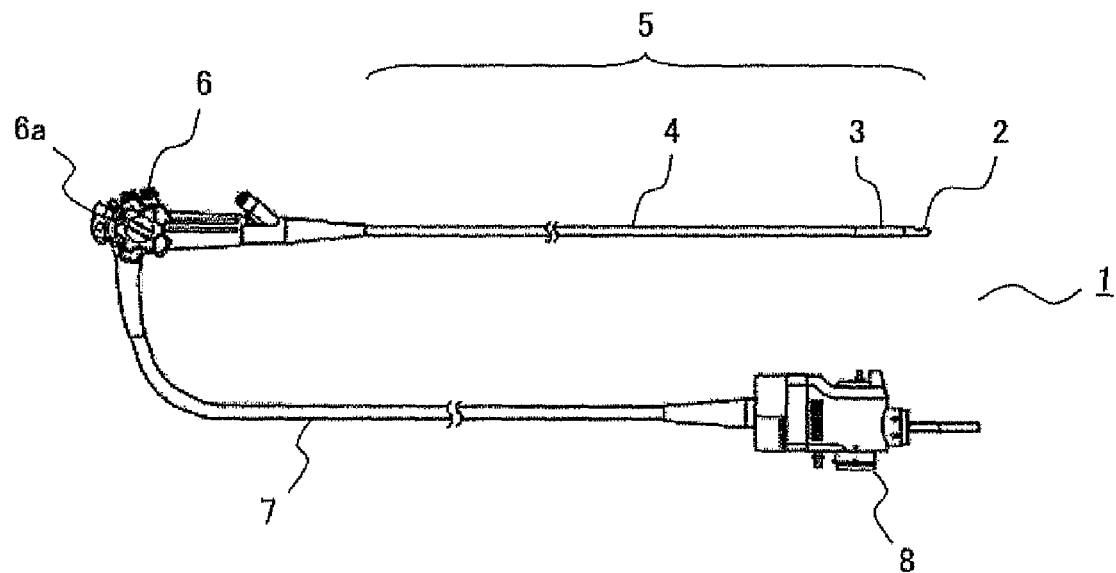
F I G. 1

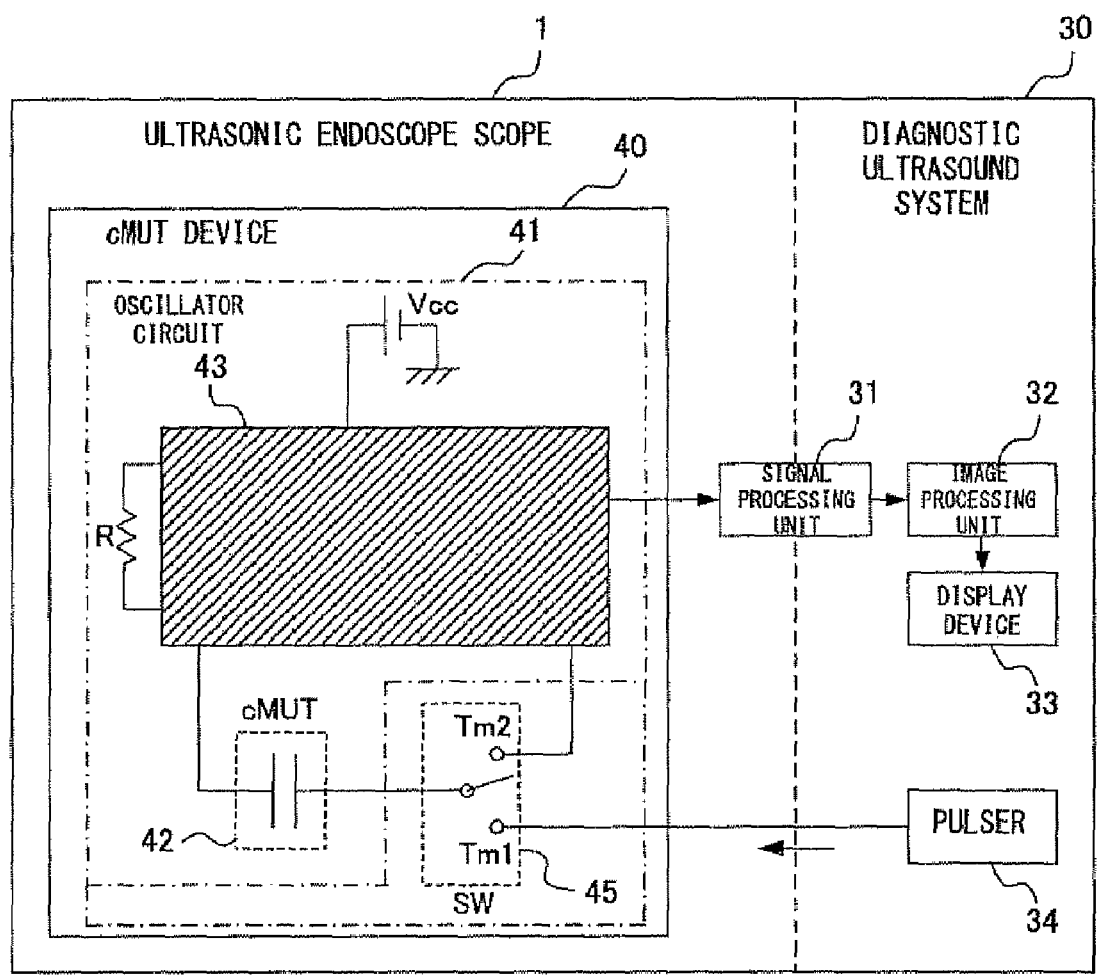
F I G. 3

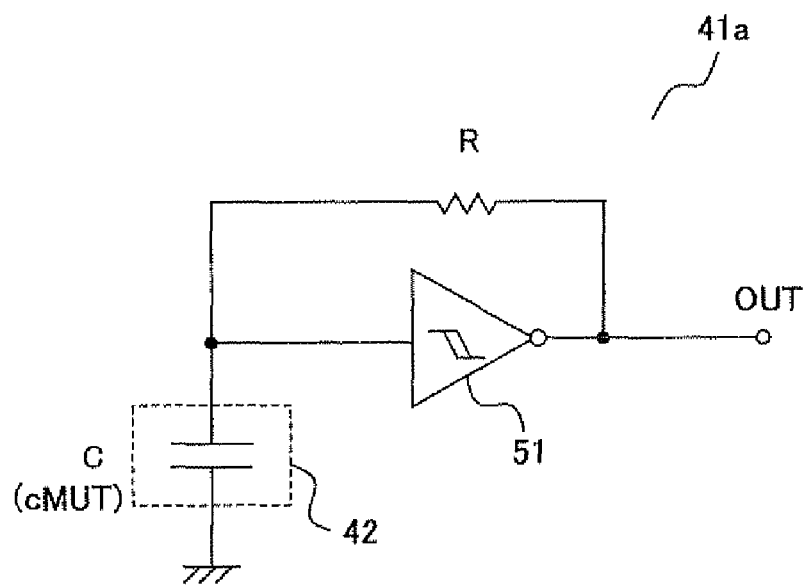
F I G. 4

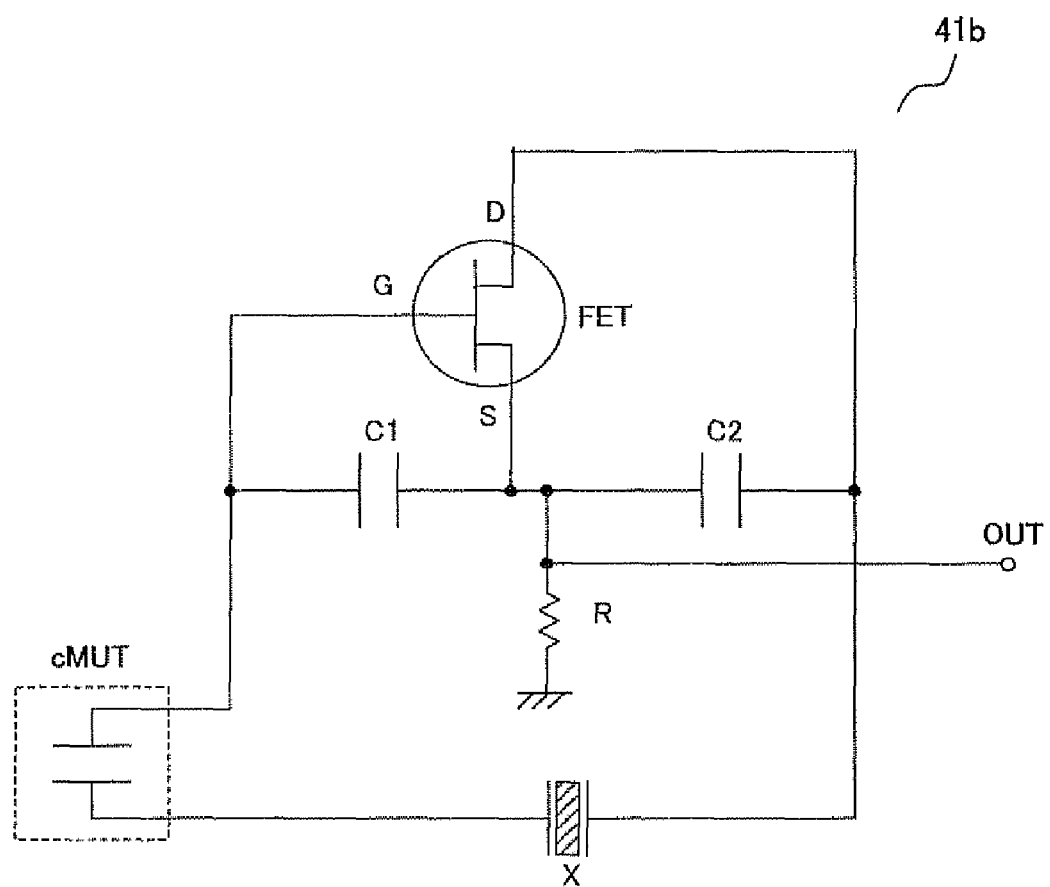
F I G. 6

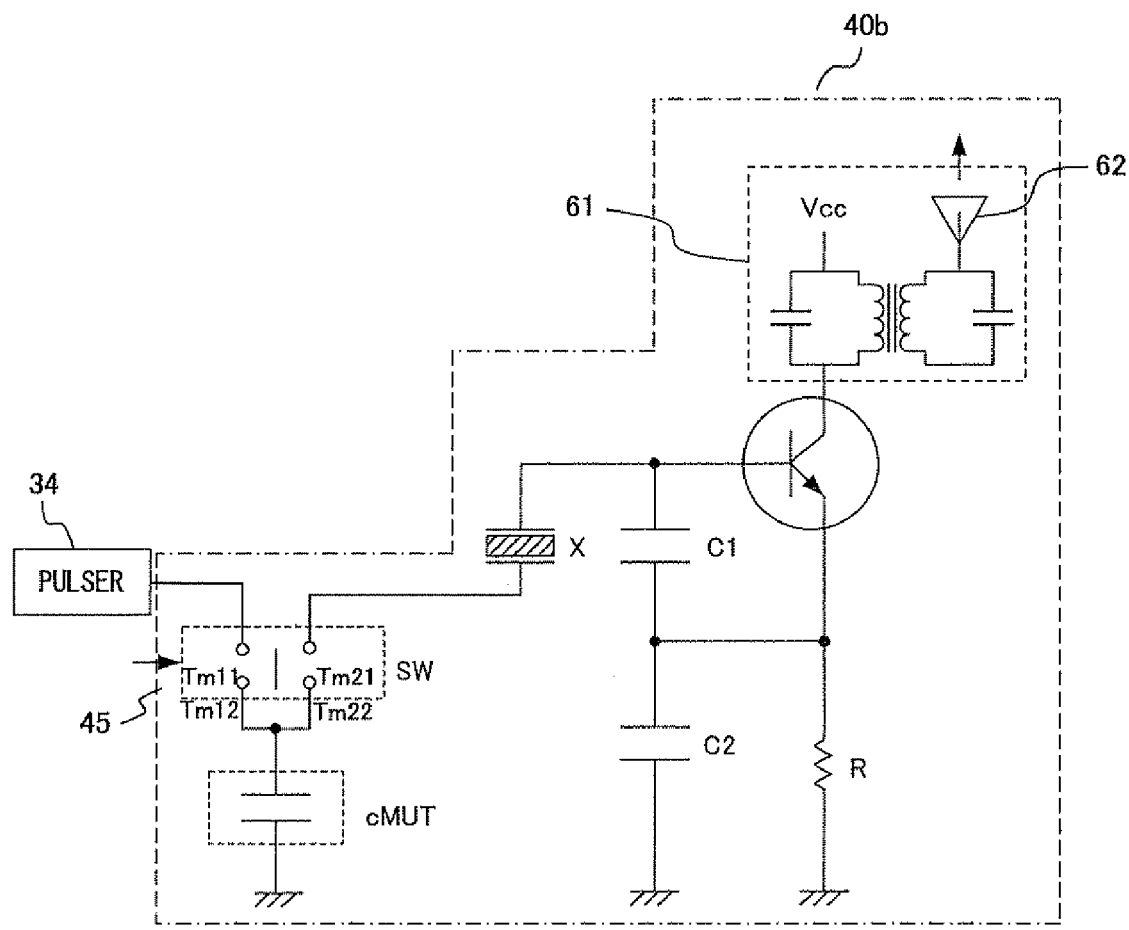
F I G. 8

CAPACITIVE MICROMACHINED ULTRASONIC TRANSDUCER (CMUT) DEVICE AND IN-BODY-CAVITY DIAGNOSTIC ULTRASOUND SYSTEM

CROSS REFERENCE TO RELATED APPLICATION

This application is based on and claims the benefit of priority from the prior Japanese Patent Application No. 2007-87769 filed in Japan on Mar. 29, 2007, the entire contents of which are incorporated by this reference.

BACKGROUND OF THE INVENTION

1. Field of the Invention

The present invention relates to transmission and reception of the ultrasound performed by using a capacitive micromachined ultrasonic transducer (cMUT) that is manufactured by using the micromachine process.

2. Description of the Related Art

The diagnostic ultrasound method has been attracting interest, in which the ultrasound is transmitted in a body cavity, the echo signals of the transmitted ultrasound is used to visualize the state of the body cavity in order to use the image for the making a diagnosis. One of the instruments that are used for this diagnostic ultrasound method is an ultrasonic endoscope. The ultrasonic endoscope has an ultrasonic transducer at the distal end of the insertion tube that is to be inserted into body cavities. This ultrasonic transducer can convert electric signals into ultrasonic beams in order to transmit the beams in the body cavities, and can receive the ultrasonic beams reflected in the body cavities in order to convert the received ultrasonic beams into electric signals. By performing the imaging process on the basis of these electric signals, ultrasonic images can be obtained.

In recent years, capacitive micromachined ultrasonic transducers (cMUT) that are obtained by silicon semiconductor processing by using the MEMS (Micro Electro-Mechanical System) technique have been attracting interest.

The cMUT is a device that has a bottom electrode arranged on a silicon substrate and an upper electrode on a membrane spaced from the bottom electrode by a cavity. When an RE signal is transmitted to one of the electrodes of the cMUT, a membrane including the upper electrode vibrates and generates the ultrasound.

It is said that the direct-current (DC) bias voltage is usually required to perform the transmission and reception of the ultrasound that uses the cMUT (as disclosed in International Publication Wo 2003/011749). The reason why the DC bias voltage is used for the transmission and reception of the ultrasound by using the cMUT is described below.

The object of using the DC bias voltage for transmitting the ultrasound is to cause the membrane to express the change of the waveform that is the same as that of the driving signal. When a high-frequency pulse signal (RF signal) is applied to the cMUT as a driving signal, the two electrodes only attract each other and will not repel each other because they are respectively charged with the electric charges that have opposite polarities. Accordingly, even when a signal having the sine wave is input as the RF signal, the membrane of the cMUT vibrates and deforms only in such a manner that the distance between the electrodes becomes shorter. Accordingly, the output vibration waveform does not correspond to the waveform of the input RF signal, and is distorted. Also, because the membrane vibrates and deforms only in such a manner that the distance between the electrodes becomes shorter, the amplitude becomes ½ with respect to the waveform of the input RF signal. Also, the frequency of the transmitted waveform becomes twice. Then, by applying a prescribed DC bias voltage to the input RF signal (sine wave), the distortion of the amplitude of the sine wave can be suppressed. Thereby, the transmission waveform from the cMUT can be caused to correspond to the distortion of the same waveform as the RF signal.

However, voltages that are relatively high (for example, 100V) are continuously applied as the DC bias voltage and the RF signal, accordingly the operation effective voltage becomes high. Also, when a type of a cMUT that is inserted into body cavities is considered, the outer dimensions are limited, which is different from a type of a cMUT that is used out of the body, thus has to be small. Accordingly, the applicants of this application disclosed a technique of operating a cMUT by applying a driving pulse signal obtained by superposing a DC pulse signal on an RF signal (International Publication: WO 2005/120359).

The object of using the DC bias voltage on receiving the ultrasound is to detect $\Delta V$ that is based on $\Delta V = Q/\Delta C$ where $\Delta C$ is change of the capacitance occurring when the membrane of the cHUT (upper electrode) receives ultrasound with the upper and bottom electrodes being charged. By detecting this change of the charge, the received ultrasound can be converted into electric signals. As described above, in the conventional configuration, a constant charge $Q$ (=CV, C:Capacitance without receiving ultrasound, V:DC bias voltage) that was accumulated in an electrode constituting the cMUT by using the DC bias voltage and the voltage $\Delta V = Q/\Delta C$ (calculation based on the capacitance change $\Delta C$ that is accompanied with the change of the distance between the electrodes caused by the reception of the ultrasound) was detected by using a charge amplifier. Then, the impedance conversion and the voltage amplification are achieved. And the voltage output signal corresponds to the receiving ultrasonic signal, and diagnostic ultrasound images are obtained after the signal processing and image processing.

Conventional documents that relate to the present invention include Japanese Patent Application Publication Nos. 2003-294527, 2005-265432, and 2001-339796.

SUMMARY OF THE INVENTION

The cMUT device according to the present invention comprises:

a cMUT obtained by processing a silicon substrate by using a silicon micromachining technique; and an oscillator circuit having the cMUT as a capacitor, and outputting a frequency modulation signal obtained by modulating a frequency of an oscillation signal to be output on the basis of a change of capacitance of the cMUT.

The in-body-cavity diagnostic ultrasound system, comprises:

a cMUT obtained by a technology of Silicon micromachine; and an oscillator circuit having the cMUT as a capacitor, and outputting a frequency modulation (FM) signal by modulating a frequency of an oscillation signal to be output on the basis of a change of capacitance of the cMUT.

BRIEF DESCRIPTION OF THE DRAWINGS

FIG. 1 shows an outline configuration of an ultrasonic endoscope scope 1 in an embodiment of the present invention;

FIG. 3 shows the principle of an in-body-cavity diagnostic ultrasound system according to an embodiment of the present invention;

FIG. 4 shows the principle of a Schmidt Trigger oscillator circuit 41a according to a first embodiment of the present invention;

FIG. 6 shows the principle of a Colpitts oscillator circuit according to a second embodiment of the present invention;

FIG. 8 shows an outline of the operation principle of the in-body-cavity diagnostic ultrasound system that transmits, in a wireless manner, to a diagnostic ultrasound system 30 the FM signals that were modulated on the basis of the received ultrasound in the second embodiment (variation);

DESCRIPTION OF THE PREFERRED EMBODIMENTS

Figure 2:
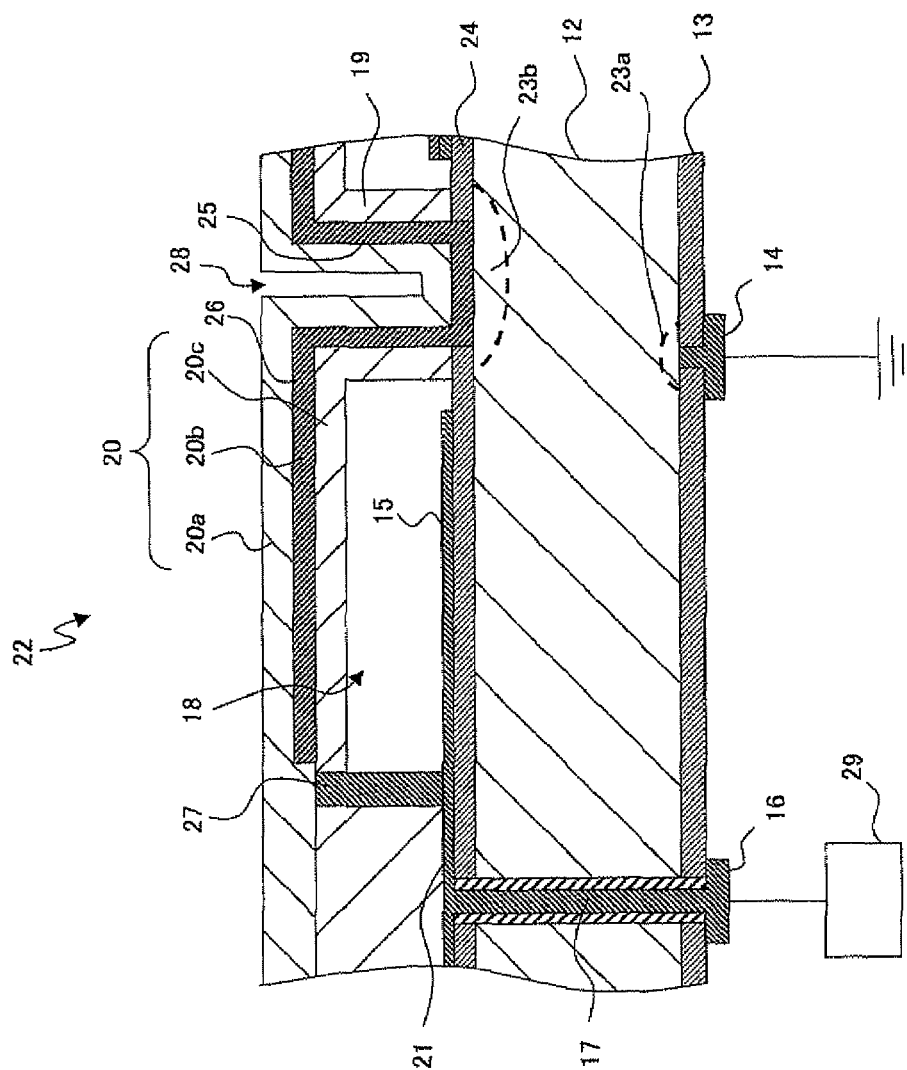
FIG. 2 shows an example of a fundamental configuration of a cMUT 2 according to an embodiment of the present invention.

As described above, direct-current (DC) bias voltage is required to perform the transmission and reception of the ultrasound by using a cMUT. In the case of the transmission of ultrasound, it is possible to attain the effect of the DC bias voltage by superposing the DC pulses that are obtained by superposing, on an RF pulse used for the transmission of ultrasound, a pulse wave having a pulse width longer than that of the RF pulse (International Publication: WO 2005/120359).

However, when receiving the ultrasound, because the pulse echo signal period is much longer than the transmission pulse signal transmission period, there is a problem that the method of superposing the DC pulses cannot be used. The period of transmission pulse signal is only several μ seconds, while the reception period for the pulse echo signal is long (for example, from 0.1 m second to 1.0 m second). The influence of the effective voltage is very little even when the transmission pulse voltage is several hundred volts if the transmission pulse signal transmission period is only several μ seconds. However, to continuously apply the DC voltage of several hundreds volts during the reception period of the pulse echo signals that are about 0.1 m second through 1.0 m second is not preferable because the effective value of the driving voltage becomes too high.

Also, as described above, a reception circuit having such functions as the conversion from charge to voltage signal, the impedance conversion, and the amplification are required. However, because the cMUT is inserted into body cavities being attached to the distal end of an ultrasonic endoscope, the distal end is desired to be as small as possible. Accordingly, the reception circuit for the cMUT is also desired to be small.

As an example in an embodiment of the present invention, a capacitive transducer will be explained, which does not require a high level of DC bias voltage for receiving ultrasound and also does not require a charge convertor to voltage, an amplifier or an impedance conversion.

FIG. 1 shows an outline configuration of an ultrasonic endoscope scope 1 in an embodiment of the present invention. The ultrasonic endoscope 1 includes an insertion tube 5 that is elongate to be inserted into body cavities, a control section 6 used for controlling the insertion tube 5, and a scope connector 8. A universal code 7 to be connected to a light source (not shown) extends from a sidewall of the control section 6, and the control section 6 and the scope connector 8 are connected with each other. Also, the scope connector 8 is connected to a diagnostic ultrasound system (not shown).

The insertion tube 5 has a cMUT 2, a bending section 3 that can arbitrarily be bent, and a flexible tube 4 that are connected to each other. The control section 6 has an angulation control knob 6a. The angulation control knob 6a is operated in order to bend the bending section 3.

Also, the distal end of the insertion tube 5 has an illumination lens cover that constitutes an illumination optical unit for emitting illumination light to the observed sites, an observation lens cover that constitutes an observation optical system for capturing optical images of the observed sites, and an instrument channel port that is an opening from which instruments are projected, and the like (all of these components are not shown).

FIG. 2 shows an example of a configuration of the cMUT 2 according to an embodiment of the present invention. The cMUT 2 is a transducer that is obtained by a silicon processing by using the silicon micromachining technique. The cMUT 2 employs a configuration in which units each consisting of a plurality of transducer elements serving as the minimum unit for inputting and outputting the drive control signals are arrayed (cMUT array). Each transducer element includes a large number of cMUT cells.

A transducer cell 22 employs a configuration in which an upper electrode 20b and a bottom electrode 15 spaced apart by a cavity 18. The detailed configuration of the transducer cell 22 is explained by referring to FIG. 2.

The transducer cell 22 includes a silicon substrate 12, a first insulation film 24, a back insulation film 13, an ohmic contact regions 23a and 23b, a ground electrode pad 14, an electrode pad for signal in/out 16, a bottom electrode 15, a bottom electrode wiring 21, a wafer piercing wiring 17, a membrane supporter 19, a via-wiring 25, an upper electrode wiring 26, a membrane 20 (a protection film 20a, an upper electrode 20b, and a second insulation film 20c), a cavity 18, a plug 27, and an element boundary trench 28.

The membrane 20 is defined as a vibration film that consists of a layer made of the protection film 20a, the upper electrode 20b, and the second insulation film 20c, and is supported by the membrane supporter 19. The first insulation film 24 is formed on the top surface of the silicon substrate 12, and the bottom electrode 15 is formed on the first insulation film 24. It is also possible to employ a configuration in which an insulation film is additionally formed on the bottom electrode 15.

On the back surface of the silicon substrate 12, the electrode pad for signal in/out 16 serving as a continuation terminal for the bottom electrode 15, and a signal electrode pad serving as a continuation terminal for the upper electrode 20b (i.e., the ground electrode pad 14) are provided. The ground electrode pad 14 and the electrode pad for signal in/out 16 are insulated from each other by the insulation film 13 formed on the back surface of the silicon substrate 12.

The electrode pad for signal in/out 16 is electrically interconnect with the bottom electrode 15 via the electrode 17 formed in a wafer piercing via hole that pierces the silicon substrate (wafer piercing wiring) and the bottom electrode wiring 21. Driving signals are input to the electrode pad for signal in/out 16 from a transmission reception circuit 29, and, the reception signals are transmitted from the electrode pad for signal in/out 16.

The upper electrode 20b is electrically continuous, via the upper electrode wiring 26 and the via-wiring 25, with the ohmic contact region 23b formed on the silicon substrate 12, and is further electrically continuous with the ground electrode pad 14 via the ohmic contact regions 23a and 23b.

Also, the neighboring transducer elements each consisting of a plurality of the transducer cells are separated from each other by the element boundary trenches 28. The plug 27 is a component that is used for plugging a sacrifice layer removal hole formed when the cavity 18 is formed in a production step.

The operations of the transducer elements will be explained. The membrane 20 vibrates when the upper electrode 20b and the bottom electrode 15 are caused to attract each other and return to the original positions by the pulse signals applied to the upper electrode 20b and the bottom electrode 15. This vibration causes the membrane 20 to transmit ultrasound from the surface.

The above configuration is employed when only the cMUT is formed on the Si substrate. When an oscillator circuit used for the ultrasound reception is also formed on the cMUT in a monolithic manner, a pad for the DC power source terminal to the oscillator circuit, a ground pad, a pad for reception signal transmission, a pad for a transmission driving signal, and a transmission/reception SW control signal transmission pad are required.

FIG. 3 shows the principle of an in-body-cavity diagnostic ultrasound system according to an embodiment of the present invention. FIG. 3 schematically shows the in-body-cavity diagnostic ultrasound system that includes a cMUT 42 attached to the distal end of the ultrasonic endoscope scope 1, a cMUT device 40 including the peripheral circuits for the cMUT 42, and a diagnostic ultrasound system 30.

The diagnostic ultrasound system 30 includes a signal processing unit 31, an image processing unit 32, a display device 33, and a pulser 34. The pulser 34 is a pulse generation circuit for generating driving signals for driving the cMUT (cMUT element) 42 when transmitting the ultrasound, and creates, as the driving signals, the RF pulse signals that are superposed on the DC pulse signals (International Publication: WO 2005/120359).

The cMUT 40 includes an oscillator circuit 41 and a switch (SW) 45. The oscillator circuit 41 is driven when the ultrasound is received, and the capacitor as the constituent thereof is replaced with the cMUT 42. The portion denoted by numeral 43 represents a circuit element that determines the vibration frequency, i.e., the constituent that is other than the cMUT 42 and a DC resistor R. "$V_{cc}$" denotes a DC voltage used for driving the oscillator circuit 41.

The transmission/reception switch (hereinafter, referred to as a "SW") 45 switches the circuits to be used for the transmission and the reception of the ultrasound in accordance with the transmission/reception switching signals transmitted from the diagnostic ultrasound system, and selects a terminal Tm1 when transmitting ultrasound and selects a terminal Tm2 when receiving ultrasound.

Here, the operations of the oscillator circuit 41 will be explained. When the capacitance of the oscillator circuit i.e., the capacitance of the cMUT 42 is $C_0$, the oscillation frequency f of the oscillator circuit 41 without receiving ultrasound is determined by the capacitance C and the DC resistance R. Because R is a constant value, the oscillation frequency f is also constant if C is constant. Accordingly, the oscillation output has not undergone any change.

When the cMUT receives ultrasound, the membrane 20 vibrates, accordingly, the distance between the upper electrode 20b and the bottom electrode 15 changes, and the capacitance C of the cMUT 42 also changes in accordance with the equation $C=C_0(1+A \sin \omega t)$. In the change $\Delta C$ of the capacitance C of the cMUT, $C_0$ changes in proportion to the sound pressure of the acoustic wave (ultrasound) that is received by the membrane.

As described above, the oscillation frequency f of the oscillator circuit 41 is determined by the capacitance C, accordingly, when the capacitance C changes, the oscillation frequency f also changes. In other words, the oscillation signals are subject to the frequency modulation. The amount of the change of this frequency is proportional to the ultrasound pressure that is received by the membrane.

Accordingly, when receiving ultrasound, the oscillator circuit 41 performs the frequency modulation (FM) on the output signal that has the oscillation frequency f of the oscillator circuit, and outputs this FM signal to the signal processing unit 31.

The signal processing unit 31 is provided in the ultrasonic endoscope scope 1 or in the diagnostic ultrasound system 30 or between them for performing various kinds of signal processing. The pulser 34 is included in the signal processing unit. One of the functions that the signal processing unit 31 has is to convert the FM signal output from the signal processing unit 31 into an amplitude modulation signal (AM signal) i.e., corresponding to the reception ultrasonic signal.

The image processing unit 32 creates, by using a scan convertor or the like, image signals for the diagnostic ultrasound images from the signals processed by the signal processing unit 31. The display device 33 displays the diagnostic ultrasound image on the basis of the image signals created by the image processing unit 32.

Additionally, the oscillator circuit 41 arranged close to the cMUT has to be equipped with the DC voltage source $V_{cc}$ in order to generate vibration. This DC voltage $V_{cc}$ can be much smaller than the DC voltage shown in the International Publication WO 2005/120359, thus can be transmitted via a transmission cable.

Hereinafter, embodiments of the present invention will be explained in detail.

First Embodiment

In the present embodiment, a case is explained, in which a Schmidt Trigger oscillator circuit is used as the oscillator circuit 41. In the explanation below, the above described constituents that are also used in this embodiment will be denoted by the original symbols with "a" being added.

FIG. 4 shows the principle of a Schmidt Trigger oscillator circuit 41a. The Schmidt Trigger oscillator circuit 41a accordance with the present embodiment includes a Schmidt Trigger inverter 51, a resistor R, and a capacitor C. The capacitor C in FIG. 4 is constituted of the cMUT 42.

The Schmidt Trigger oscillator circuit 41a is an oscillator circuit whose oscillation frequency f can be expressed by $f=1/T$, T can be expressed by $T=2CR\ln((V_{cc}-V_N)/(V_{cc}-V_P))$ (where $V_{cc}$ represents the power source voltage of the Schmidt Trigger oscillator circuit 41a, $V_P$ represents the threshold voltage at which output is inverted when the input of the Schmidt Trigger inverter is changed from Low to High, $V_N$ represents the threshold voltage at which the output is inverted when the input of the Schmidt Trigger inverter changes from High to the Low), and whose output signal is a rectangular wave.

When the cMUT 42 receives ultrasound, the membrane is caused to vibrate by the sound pressure of the received ultrasound, accordingly the distance between the upper electrode and the bottom electrode in the cMUT changes, and the capacitance C changes in accordance with the equation $C=C_0(1+A \sin \omega t)$. Accordingly, the oscillation frequency is expressed by the equation $f=1/(T_0(1+A \sin \omega t))$. Consequently the oscillation frequency is modulated. Here, $T_0=2C_0R\ln((V_{cc}-V_N)/(V_{cc}-V_P))$.

As described above, the Schmidt Trigger oscillator circuit 41a outputs the oscillation signal that has undergone the frequency modulation (FM) on the basis of the ultrasound received by the cMUT 42.

Figure 5:
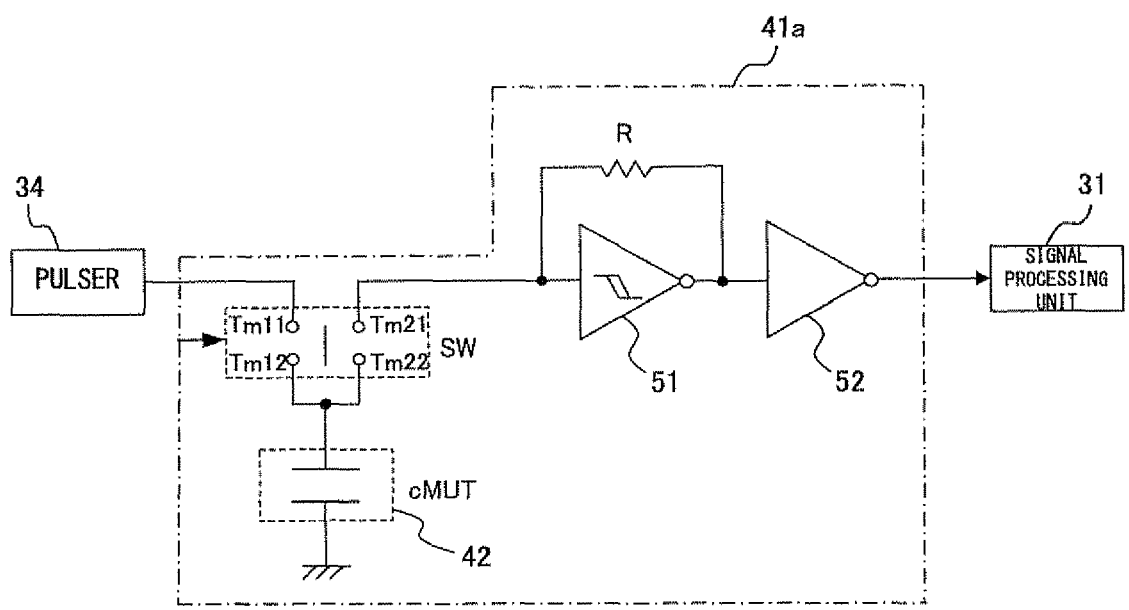
FIG. 5 shows an outline of the operation principle of an in-body-cavity diagnostic ultrasound system that uses the Schmidt Trigger oscillator circuit 41a according to the first embodiment.

FIG. 5 shows an outline of the operation principle of an in-body-cavity diagnostic ultrasound system that uses the Schmidt Trigger oscillator circuit 41a according to the present embodiment. The Schmidt Trigger oscillator circuit 41a shown in FIG. 5 is obtained by adding a buffer circuit 52 to the output side of the Schmidt Trigger inverter 51 shown in FIG. 4.

When transmitting ultrasound, a terminal Tm11 and a terminal Tm12 of the SW 45 become electrically shorted with each other on the basis of the transmission/reception switching control signal. When an RF pulse signal superposed on a DC pulse signal output from the pulser 34 is input to the cMUT 42, ultrasound is transmitted from the cMUT 42.

When receiving ultrasound, a terminal Tm21 and a terminal Tm22 of the SW 45 become electrically shorted with each other. Then, the circuit on the side of the Schmidt Trigger oscillator circuit 41a becomes effective. When the cMUT 42 receives ultrasound, the capacitance of the cMUT 42 changes, accordingly the oscillation signal that has undergone the frequency modulation (FM signal) is output from the Schmidt Trigger oscillator circuit 41a. Additionally, because output signal of the oscillator circuit is roughly equal to the DC power source voltage $V_{cc}$, accordingly, the output signal is substantially amplified. The FM signal output from the Schmidt Trigger oscillator circuit 41a is input to the signal processing unit 31. The processes that will be performed thereafter are the same as those explained in FIG. 3.

According to the present embodiment, the ultrasound reception signal can be detected on the basis of the change of the capacitance of the cMUT, accordingly it is not necessary to apply the DC bias voltage. Also, the impedance conversion is not necessary either, accordingly the amplified signal can be output at a power source voltage level of the oscillator circuit. Further, the signal output from the oscillator circuit is an FM signal, the S/N ratio is excellent.

Second Embodiment

In the present embodiment, a Colpitts oscillator circuit is used as the oscillator circuit 41. In the explanation hereinbelow, the above described constituents that are also used in this embodiment will be denoted by the original symbols with "b" being added.

FIG. 6 shows the principle of a Colpitts oscillator circuit according to the present embodiment. A Colpitts circuit 41b in FIG. 6 employs a configuration in which a coil L of a standard Colpitts oscillator circuit is replaced with a series circuit of a piezoelectric device X and a cMUT.

The piezoelectric device has the impedance characteristic of resonance/anti-resonance. And the piezoelectric device has the characteristic of the coil L over the frequency band between the resonance frequency fr and the anti-resonance frequency fa, thus can vibrate in this band.

Accordingly, the capacitance C of the cMUT changes, thus the oscillation signal thereof is modulated. Then, the modulated oscillation frequency is controlled to be in the band between the resonance frequency fr and the anti-resonance frequency fa.

Additionally, as the piezoelectric device, devices such as a crystal oscillator or a ceramics oscillator are used. Also, in FIG. 6, an FET (field effect transistor) is used, however, a bipolar transistor Tr can be used.

Figure 7:
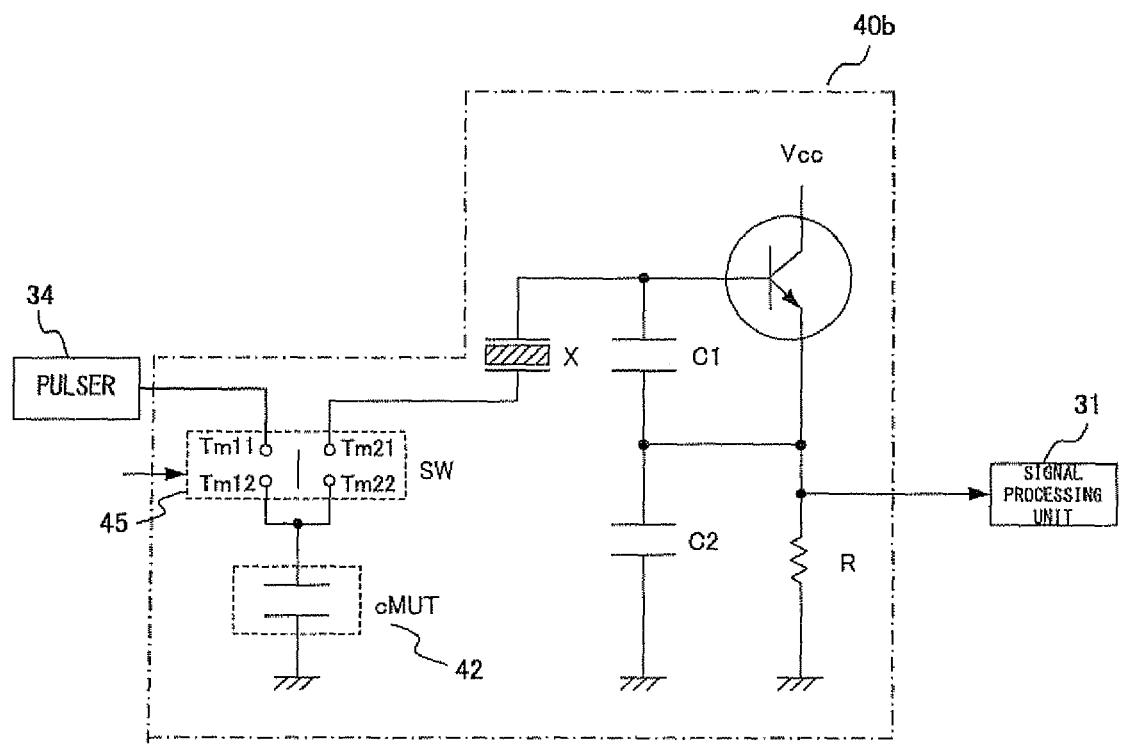
FIG. 7 shows an outline of the principle of the in-body-cavity diagnostic ultrasound system in which the Colpitts circuit 41b according to the second embodiment of the present invention is used.

FIG. 7 shows an outline of the principle of the in-body-cavity diagnostic ultrasound system in which the Colpitts circuit 41b according to the present embodiment is used. In the configuration of FIG. 7, the bipolar transistor Tr is used instead of an FET.

When transmitting ultrasound, the terminal Tm11 and the terminal Tm12 of the SW 45 become electrically shorted with each other in accordance with the transmission/reception switching control signal. At this moment, when the pulse signal that is obtained by superposing the RF pulse signal on the DC pulse signal output from the pulser 34 is input to the cMUT 42, the cMUT 42 transmits ultrasound.

When receiving ultrasound, the terminal Tm21 and the terminal Tm22 of the SW45 become electrically shorted with each other in accordance with the transmission/reception switching control signal. Then, the circuit on the side of the Colpitts circuit 41b becomes effective. When the cMUT 42 receives ultrasound, the capacitance of the cMUT 42 changes, and the oscillation signal that has undergone the frequency modulation (FM signal) is output from the Colpitts circuit 41b. Additionally, this output signal is also amplified due to the operation of the oscillator circuit. The FM signal output from the Colpitts circuit 41b is output to the signal processing unit 31. The processes that will be performed thereafter are the same as those explained in FIG. 3.

FIG. 8 shows, as a variation of FIG. 7, an outline of the operation principle of the in-body cavity diagnostic ultrasound system that transmits, in a wireless manner, to the diagnostic ultrasound system 30 the FM signals that were modulated on the basis of the received ultrasound. The configuration shown in FIG. 8 is obtained by adding, to the configuration shown in FIG. 7, a transmission circuit 61 for transmitting only a prescribed high-frequency wave to a point between the collector of the transistor Tr and the power source voltage $V_{cc}$ via an antenna 62.

In the transmission circuit 61, a LC resonance circuit is arranged on the side of the collector of the transistor Tr, and this L is used as an electromagnetic transformer, and the LC resonance circuit that has the antenna 62 via the transformer coupling is arranged. By this configuration, the FM signal output from the Colpitts oscillator circuit can be transmitted to the diagnostic ultrasound system 30 having a reception antenna (not shown) via the antenna 62. Also, by setting the resonance frequency of the LC resonance circuit to be an integral multiple of the center frequency of the received ultrasound, only the non-linear components of the ultrasound can be extracted, and the extracted components can be used in the non-linear ultrasound imaging.

Because the diagnostic ultrasound system that receives the above FM signal has a local oscillator circuit, a filter, a mixer, a demodulation circuit, and the like, the received FM signal is demodulated by using these circuits. This demodulation will later be explained in detail.

According to the present embodiment, ultrasonic reception signal can be detected on the basis of the change of the capacitance of the cMUT, accordingly it is not necessary to apply a high DC bias voltage in addition to the DC power source voltage $V_{cc}$ being at a low level. Also, the impedance conversion is not necessary, thus the amplified signal can be output at the power source voltage level of the oscillator circuit. Further, the signals output from the oscillator circuit are the FM signals, accordingly the S/N ratio is excellent.

Third Embodiment

In the present embodiment, a case is explained, in which a Wien bridge oscillator circuit is used as the oscillator circuit 41. In the explanation hereinbelow, the above described constituents that are also used in this embodiment will be denoted by the original symbols with "c" being added.

Figure 9:
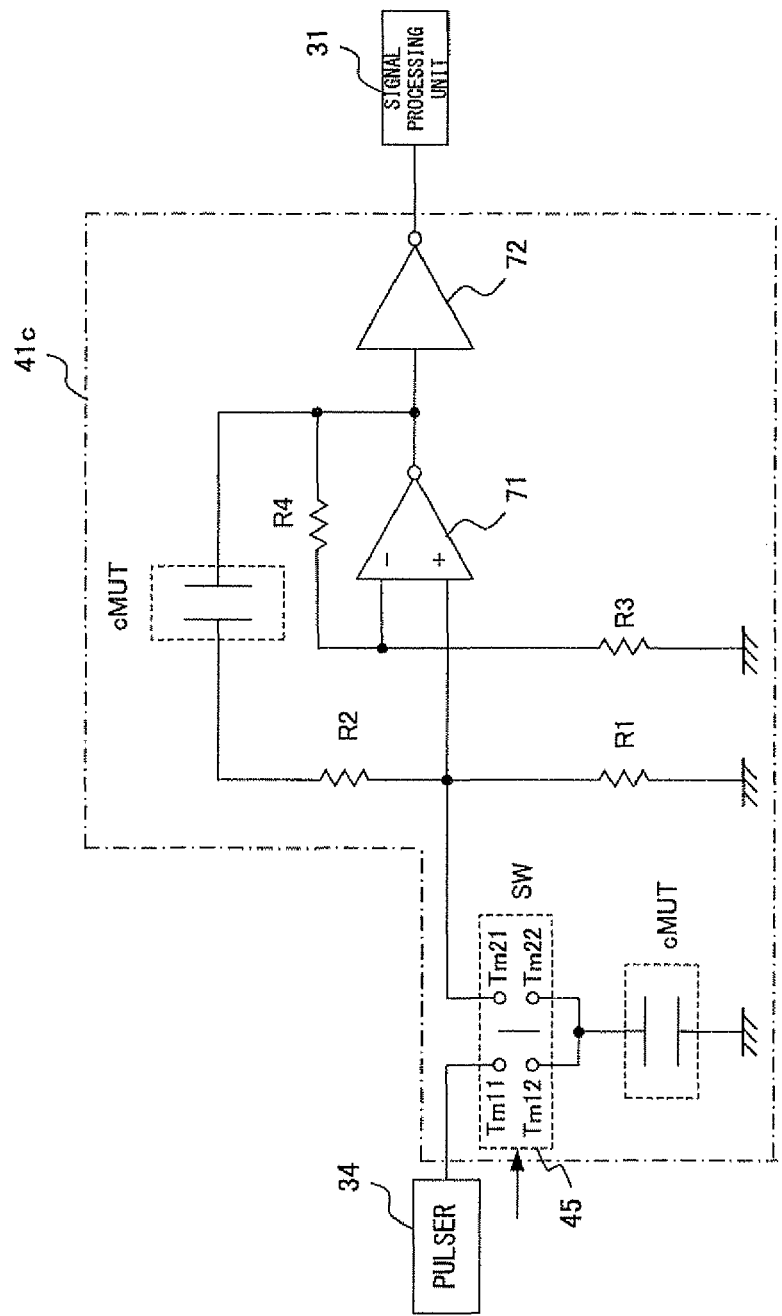
FIG. 9 shows an outline of the operation principle of the in-body-cavity diagnostic ultrasound system in which a Wien bridge oscillator circuit 41c according to a third embodiment of the present invention is used.

FIG. 9 shows an outline of the operation principle of the in-body-cavity diagnostic ultrasound system in which a Wien bridge oscillator circuit 41c according to the present embodiment is used. FIG. 9 shows a fundamental Wien bridge oscillator circuit that is a sine wave generator circuit in which C and R are connected to an operational amplifier 71. When C=C1=C2 and R=R1=R2, the oscillation frequency f can be expressed as $f=1/(2\pi CR)$. Numeral 72 denotes a buffer circuit.

In the present embodiment, one or both of capacitors C1 and C2 are replaced with a cMUT. Accordingly, when the cMUT receives ultrasound, the sine wave oscillation output that has undergone the frequency modulation is obtained in accordance with the change of the capacitance. The operations to be performed thereafter are the same as those in the above embodiments, therefor the explanation thereof will be omitted. Additionally, the oscillation output voltage is an operation voltage level of ICs or operation amplifiers, and may be around the operation voltage of a cMOS inverter IC used for generating clock signals.

According to the present embodiment, ultrasound reception signals can be detected on the basis of the change of the capacitance of the cMUT, accordingly it is not necessary to apply a high DC bias voltage in addition to the DC power source voltage $V_{cc}$ being at a low level. Also, the impedance conversion is not necessary, thus the amplified signal can be output at the power source voltage level of the oscillator circuit. Further, the signals output from the oscillator circuit are the FM signals, accordingly the S/N ratio is excellent.

Fourth Embodiment

In the present embodiment, a case in which the oscillator circuit 41 is used as the cMUT array is explained. The oscillator circuit 41 used in the present embodiment may be not only the oscillator circuits 41a, 41b, and 41c in the first through third embodiments, but also may be a CR oscillator circuit and a LC oscillator circuit that are primary factors for determining the oscillation frequency.

Figure 10:
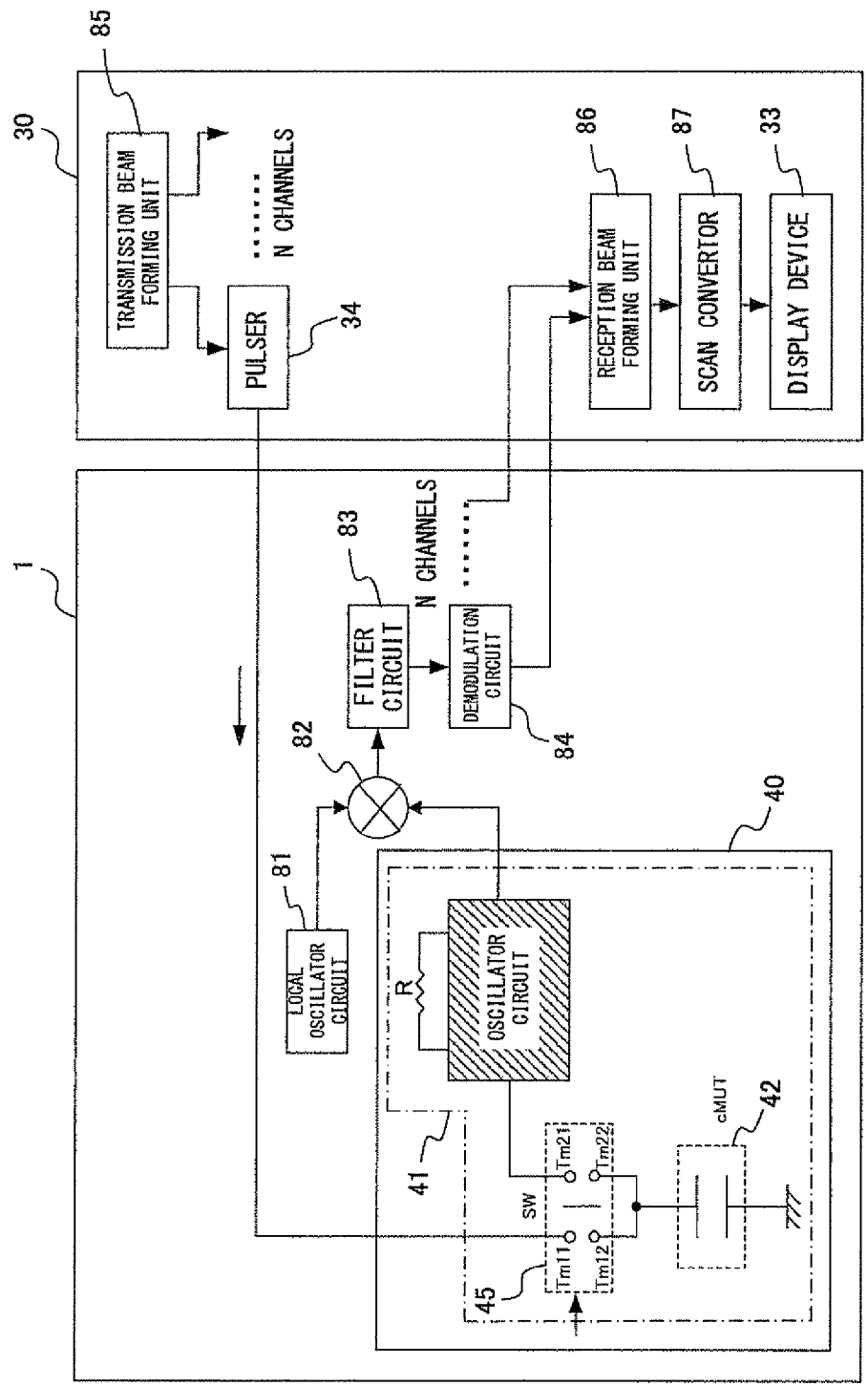
FIG. 10 shows an outline of the operation principle of the in-body-cavity diagnostic ultrasound system that includes a cMUT array according to a fourth embodiment of the present invention.

FIG. 10 shows an outline of the operation principle of the in-body-cavity diagnostic ultrasound system that includes the cMUT array according to the present embodiment. On the side of the ultrasonic endoscope 1, the cMUT device 40, a local oscillator circuit 81, a mixer 82, a filter circuit 83, and a demodulation circuit 84 are provided. On the side of the diagnostic ultrasound system 30, a transmission beam forming unit 85, the pulser 34, a reception beam forming unit 86, a scan convertor 87, and the display device 33 are provided.

When transmitting ultrasound, the terminal Tm11 and the terminal tm12 of the SW 45 become electrically continuous with each other in accordance with the transmission/reception switching control signal.

The reception beam forming unit 86 outputs to the pulser 34 a signal used for controlling the beam scanning performed by using the ultrasound transmitted from the cMUT. At this moment, as many signals as the number of N channels are respectively transmitted from the reception beam forming unit 86 to the corresponding pulsers 34. The number of N channels corresponds to the number of the cMUT elements that constitute the cMUT array. Accordingly, there are as many groups each consisting of the pulser 34, the oscillator circuit 41, the local oscillator circuit 81, the mixer 82, the filter 83, and the demodulation circuit 84 as the number of the N channels (the number of the cMUT elements).

The pulser 34 generates the pulse signal that is obtained by superposing the RF pulse signal on the DC pulse signal on the basis of the control signal output from the demodulation circuit 84, and outputs this generated signal to the cMUT 42 via the SW 45. The respective cMUT elements transmit ultrasound on the basis of the pulse signals that are obtained by superposing the RF pulse signal on the DC signal.

When receiving ultrasound, the terminal Tm21 and the terminal Tm22 of the SW 45 become electrically shorted with each other. Then, the circuit on the side of the oscillator circuit 41 becomes effective. When the cMUT 42 receives ultrasound, the capacitance of the cMUT 42 changes, accordingly an oscillation signal that has undergone the frequency modulation (FM signal) is output from, for example, the Schmidt Trigger oscillator circuit 41a. Additionally, due to the operation of the oscillator circuit, the output signal thereof is substantially amplified.

As the FM signal output from the cMUT device 40, an intermediate frequency signal (for example, 10.7 MHz) that is the frequency component of the difference between the local oscillation frequency and the frequency of the input FM signal is obtained by using the local oscillator circuit 81 and the mixer 82. The FM signal that has undergone the frequency conversion passes through the filter circuit 83, and the noise components are removed. In other words, the filter circuit 83 is used for passing the FM signal whose center frequency is 10.7 MHz and for removing the noise that is out of the desirable band. An example of this filter circuit 83 is a piezoelectric filter. The signal output from the filter circuit 83 is converted into an AM signal by the demodulation circuit 84 and is demodulated. Additionally, the reason for using the above described intermediate frequency (10.7 MHz) is that this frequency is the frequency used for the FM tuner circuit for radio receivers, the integration of the signal processing circuits has enough advanced, thus the existing IC designing techniques can be used. This fact can also be applied to the intermediate frequency for TV broadcasting (4.5 MHz).

The AM signal obtained for each channel is input to the reception beam forming unit 86. In the reception beam forming unit 86, the AM signals received from the respective channels are synthesized. The scan convertor 87 functions as the image processing unit 32, and forms diagnostic ultrasound images on the basis of the ultrasound reception signals synthesized in the reception beam forming unit 86 in order to cause the display device 33 to display the formed diagnostic ultrasound images.

Additionally, the oscillator circuit 41 may be formed, in a monolithic manner, close to the cMUT elements formed on a semiconductor substrate. Further, also the pulser 34, the SW 45, the local oscillator circuit 81, the mixer 82, the filter circuit 83, and the demodulation circuit 84 may be formed close to the cMUT elements in a monolithic manner.

According to the present invention, the cMUT device formed by using the cMUT is used as a capacitor for the oscillator circuit, thereby it is possible to detect, as the change of the frequency of the oscillation signal, the change of the capacitance caused by external factors such as the temperature, the pressure, the sound wave (ultrasound), or the like, to discriminate the detection signal (frequency modulation signal), and to sense the states of the temperature, the pressure, the sound wave, (ultrasound) or the like on the basis of the discrimination signal. Accordingly, DC bias voltage is not required for receiving ultrasound, and it is possible to construct an ultrasound reception system that can receive ultrasound without a charge amplifier or an impedance conversion. Thus, a high level of safety in view of the electricity is attained, and only the minimum measures for the insulation are required.

The oscillator circuit used for the cMUT according to the present invention is not limited to any one of the oscillator circuits 41a, 41b, and 41c according to the first and second embodiments of the present invention. In other words, an LC oscillator circuit and a CR oscillator circuit can be used as long as the circuit is an oscillator circuit in which C is the primary component that determines the oscillation frequency.

Also, the variation of the second embodiment (FIG. 8) can be applied to any of the embodiments, and the FM signals modulated on the basis of the reception ultrasound can be transmitted to the diagnostic ultrasound system 30 in a wireless manner.

Also, in the embodiments of the present invention, the portions of the capacitor C have been replaced with the cMUT in the various oscillator circuits. However, the scope of the present invention is not limited to this configuration. The portion of the capacitor C may be replaced with, for example, a capacitive sensor or a transducer that have conventionally required DC bias voltage, such as a capacitive microphone, a capacitive pressure sensor, or a capacitive temperature sensor.

As described above, the capacitance of a cMUT is directly used instead of detecting the change of the electric charges charged by the DC bias voltage as in the conventional techniques. Thus, the high DC bias voltage is not necessary. Also, a charge amplifier or impedance conversion is not necessary, thus the amplified signals can be output at the power source voltage level of the oscillator circuit. Further, the signals output from the oscillator circuit are FM signals, thus the S/N ratio is excellent.

In any of the embodiments explained in this application, various modifications are allowed without departing from the spirit of the present invention.

What is claimed is:

1. An in-body-cavity diagnostic ultrasound system comprising:
    a capacitive micromachined ultrasonic transducer (cMUT) obtained by processing a silicon substrate by using a silicon micromachining technique;
    an oscillator circuit having the cMUT as a capacitor, and outputting a frequency modulation signal obtained by modulating a frequency of an oscillation signal to be output on the basis of a change of capacitance of the cMUT;
    a switching unit for switching between an electric connection in which a high-frequency pulse signal superposed on DC bias voltage is supplied to the cMUT, and an electric connection between the cMUT and the oscillator circuit; and
    a demodulation unit for demodulating the frequency modulation signal output from the oscillator circuit, wherein:
    when receiving ultrasound, the switching unit switches the electric connection such that an electronic connection between the cMUT and the oscillation circuit becomes effective, and when the cMUT receives ultrasound, the oscillation circuit outputs the frequency modulation signal on the basis of a change of capacitance of the cMUT,
    the demodulation unit includes a local oscillator circuit, a mixing circuit, and a bandpass filter, and
    a transducer element of the cMUT, the oscillator circuit, the switching unit, and at least one of the local oscillator circuit, the mixing circuit, and the bandpass filter are formed on one and the same semiconductor substrate.

2. The in-body-cavity diagnostic ultrasound system according to claim 1, wherein: the oscillator circuit is a CR oscillator circuit.

3. The in-body-cavity diagnostic ultrasound system according to claim 2, wherein: the oscillator circuit is a Colpitts oscillator circuit.

4. The in-body-cavity diagnostic ultrasound system according to claim 2, wherein:
    the oscillator circuit is a Schmidt Trigger oscillator circuit.

5. The in-body-cavity diagnostic ultrasound system according to claim 2, wherein:
    the oscillator circuit is a Wien bridge oscillator circuit.

6. The in-body-cavity diagnostic ultrasound system according to claim 1, further comprising: a transmission unit for transmitting, in a wireless manner, the frequency modulation signal output from the oscillator circuit.

7. The in-body-cavity diagnostic ultrasound system according to claim 1, wherein: the demodulation unit generates an intermediate frequency signal on the basis of the frequency modulation signal.

8. The in-body-cavity diagnostic ultrasound system according to claim 7, wherein:
    the intermediate frequency signal is of 10.7 MHz.

9. The in-body-cavity diagnostic ultrasound system according to claim 1, further comprising: a pulse generation unit for supplying, to the cMUT, a high-frequency pulse signal superposed on DC bias voltage.

10. The in-body-cavity diagnostic ultrasound system according to claim 1, wherein: the cMUT includes a plurality of cMUT elements being arrayed; and the in-body-cavity diagnostic ultrasound system further comprises:
    a reception beam forming unit for synthesizing respective signals obtained by demodulating, by using the demodulation unit, the frequency modulation signal output from the oscillator circuit corresponding to each of the cMUT elements;
    an image processing unit for converting into image signals the signals synthesized by the reception beam forming unit; and
    a display unit for displaying a diagnostic ultrasound image on the basis of the image signals.

11. The in-body-cavity diagnostic ultrasound system according to claim 10, further comprising:
    a transmission beam forming unit for outputting a signal for controlling scan of an ultrasonic transmission beam transmitted from each of the cMUT elements;
    a pulse generation unit for supplying, to each of the cMUT elements, a high-frequency pulse signal superposed on DC bias voltage on the basis of the output from the transmission beam forming unit; and
    a switching unit for switching an electric connection between each of the cMUT elements and the pulse generation unit corresponding to said each of the cMUT elements and an electric connection between each of the cMUT elements and the oscillator circuit corresponding to said each of the cMUT elements.

* * * * *